United States Patent [19]

King

[11] 4,282,886
[45] Aug. 11, 1981

[54] ADHESIVE BONDED POSITIVE FIXATION EPICARDIAL LEAD

[75] Inventor: Wendell L. King, North Oaks, Minn.

[73] Assignee: Medtronic, Inc., Minneapolis, Minn.

[21] Appl. No.: 93,346

[22] Filed: Nov. 13, 1979

[51] Int. Cl.³ .............................................. A61N 1/04
[52] U.S. Cl. .................................. 128/785; 128/419 P
[58] Field of Search ................................ 128/784–786, 128/419 P, 642

[56] References Cited

U.S. PATENT DOCUMENTS

| 3,253,595 | 5/1966 | Murphy, Jr. et al. | 128/785 |
| 3,543,761 | 12/1970 | Bradley | 128/784 X |
| 3,737,579 | 6/1973 | Bolduc | 128/785 |
| 4,030,508 | 6/1977 | Thalen | 128/786 |
| 4,157,710 | 6/1979 | Abitol | 128/642 |

FOREIGN PATENT DOCUMENTS 2453840  5/1976  Fed. Rep. of Germany ........... 128/785

OTHER PUBLICATIONS

Albin et al., "Electrode Fixation Using a Plastic Adhesive . . . ", Electroencephalography and Clin. Neur., Dec. 1964, vol. 17, #6, pp. 696–697.

*Primary Examiner*—Lee S. Cohen
*Attorney, Agent, or Firm*—John L. Rooney; Lew Schwartz; Joseph F. Breimayer

[57] ABSTRACT

Adhesive bonded positive fixation epicardial lead including an electrode support member for supporting an electrode and an adhesive which adheres the electrode support member and the accompanying electrode to an exterior wall of the heart. Surgical mesh can also be affixed to the electrode support member so that after decay of the adhesive, tissue ingrowth provides for adherence of the electrode support member to the tissue of the heart wall.

6 Claims, 3 Drawing Figures

ADHESIVE BONDED POSITIVE FIXATION EPICARDIAL LEAD

CROSS REFERENCES TO CO-PENDING APPLICATIONS

None.

BACKGROUND OF THE INVENTION

1. Field of the Invention

The present invention relates generally to a surgical instrument, and more particularly, pertains to an adhesive bonded positive fixation epicardial lead for connection to a pulse generator.

2. Background of the Invention

In the past, there has been a particular problem of fastening an electrode to the atrium of the heart. The atrium is a very thin fragile membrane. Prior art electrodes with hooks, screws, barbs and other structure of positive fixation to the atrium easily damaged or punctured the atrial wall. The hooks, screws, barbs and other fixation techniques of the prior art electrodes which have invaded the tissue of the atrial wall have produced thresholds which increase with time subsequently resulting in high chronic thresholds.

The present invention overcomes the disadvantages of prior art electrodes by providing an electrode which does not invade the tissue of the heart, especially the tissue of the atrial wall.

SUMMARY OF THE INVENTION

The present invention provides adhesive bonding of an electrode thereby providing positive fixation of an epicardial lead without damaging the heart or producing high chronic thresholds.

According to one embodiment of the present invention, there is provided an adhesive bonded positive fixation epicardial lead including an electrode support member, an electrode mounted within the electrode support member and extending outwardly therefrom, a quantity of adhesive mounted about the electrode on the electrode support member and extending therefrom, surgical mesh affixed to the electrode support member and extending outwardly therefrom, and a pacing lead connecting between the electrode in the electrode support member and extending outwardly therefrom and connecting to a pulse generator.

A significant aspect and feature of the present invention is that the electrode is adhesively bonded to provide positive fixation to the exterior of the heart without damaging the heart or producing high chronic thresholds. Adhesive bonding provides positive fixation with low chronic thresholds and without damaging the atrial wall. It can, in fact, even reinforce the atrial wall.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the Figures thereof and wherein.

DETAILED DESCRIPTION OF THE PREFERRED EMBODIMENT

Figure 1:
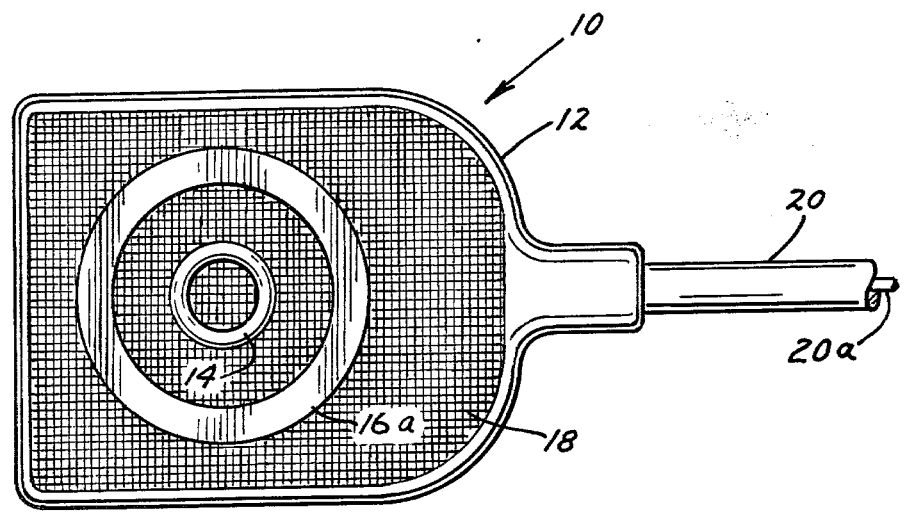
FIG. 1 is a bottom plan view of an adhesive bonded positive fixation epicardial lead, the present invention.
Figure 3:
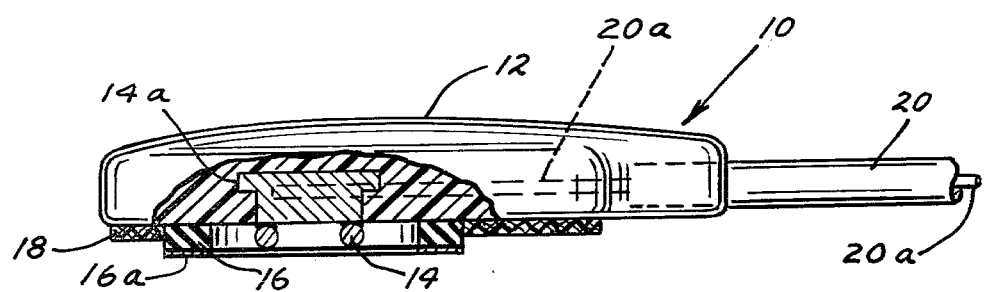
FIG. 3 is a side view of the present invention, partially in cross-section.

FIG. 1, which illustrates a bottom plan view of an adhesive bonded positive fixation epicardial lead 10, the present invention, shows a geometrical member 12, as illustrated in the figure by way of example for purposes of illustration only as a rectangular member and is not to be construed as limiting of the present invention, which is composed of polyurethane silicone or other like surgical biocompatible material. A ring electrode 14, which is by way of example for purposes of illustration only and is not to be construed as limiting of the present invention, is composed of platinum or platinum-iridium and secures to the electrode support member 12 as also illustrated in FIG. 3 and later explained in detail. The ring electrode 14 may take any other geometrical shape such as a ring, etc. depending upon the particular pacing application. An outer circumferential ring of adhesive 16, although the adhesive can take any other geometrical shape as predetermined, composed of cyanoacrylate surgical adhesive or contact adhesive surrounds the inner circumferential ring electrode 14 and is protected by a foil cover 16a. Surgical mesh 18 composed of surgical dacron material or the like attaches to the bottom of the electrode support member 12 by any known methods in the art such as adhesive, sewing, etc. and provides for tissue ingrowth into the surgical mesh 18 and long-term adhesion after the surgical adhesive 16 loses resiliency. A wire coil 20a of an insulated lead 20 connects between the electrode 14 and a connector terminal of the pacing lead not illustrated in the drawing for purposes of clarity in the illustrations.

Figure 2:
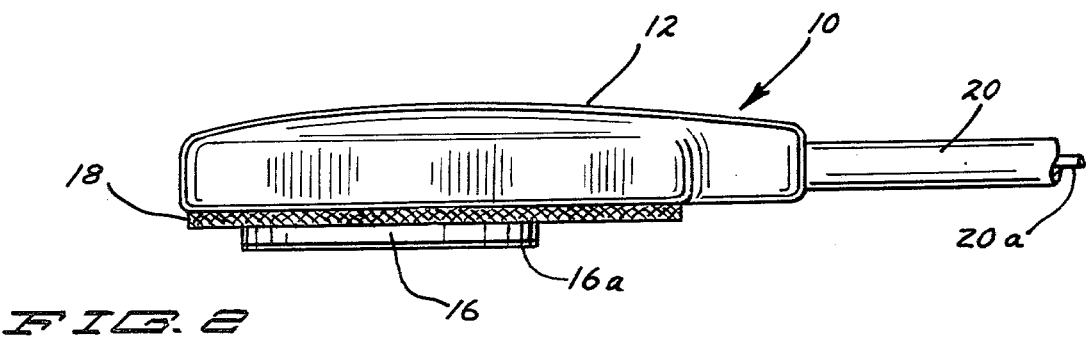
FIG. 2 is a side view of the present invention.

FIG. 2, which illustrates a side view of the invention, shows numerals corresponding to those elements previously described.

FIG. 3, which illustrates a side view partly in cross-section, shows the electrode 14 extending upwardly in a rectangular configuration including a top hat 14a for structural support and securing the electrode 14 within the electrode support member 12. The wire coil 20a secures to the electrode 14 by any known method in the art such as welding, swaging, etc. The distal end of the insulation of the lead 20 secures within the geometrical electrode support member 12.

PREFERRED MODE OF OPERATION

The adhesive bonded positive fixation epicardial lead 10 is positioned on the exterior of a heart wall and thresholds are taken. After an acceptable threshold is obtained, the exact position of the lead 10 is noted. The foil cover 16a is then peeled away from the adhesive 16 and the lead 10 is then repositioned in the exact position earlier noted. A gentle pressure is subsequently applied, and the lead 10 is bonded permanently in place to the tissue of the heart wall.

A cyanoacrylate adhesive, such as Eastman 910 would be a likely choice of adhesive 16 for the present invention. Cyanoacrylate adhesives are used as surgical adhesives to bond flesh to flesh and some of the newer contact type of adhesives would also work in this application. The adhesive can also be packaged in a separate tube and applied to the bottom of the electrode support member 12.

Various modifications can be made to the adhesive bonded positive fixation epicardial lead of the present invention without departing from the apparent scope thereof.

Having thus described the present invention, what is claimed is:

1. An electrode assembly suitable for chronic implantation within the human body comprising:
    an electrode support member of material substantially inert to body fluids;
    an epicardial electrode attached to said electrode support member;
    first means attached to said electrode support member capable of long-term adhesion of said electrode support member to body tissue for affixing said electrode support member to body tissue after a time subsequent to implantation of said electrode assembly without penetrating said body tissue; and
    second means attached to said electrode support member capable of epicardial attachment of said electrode support member for affixing said electrode support member to body tissue without penetrating said body tissue from implantation of said electrode assembly until said time subsequent to implantation of said electrode assembly, when said second affixing means loses resiliency.

2. An electrode assembly according to claim 1 wherein said first affixing means is a surgical mesh.

3. An electrode assembly according to claim 2 wherein said electrode is a ring electrode.

4. An electrode assembly according to claim 3 wherein said ring electrode is a platinum/iridium alloy.

5. An electrode assembly according to claim 1, 2, 3 or 4 wherein said second affixing means is an adhesive.

6. An electrode assembly according to claim 5 wherein said adhesive is a cyanoacrylate adhesive.

* * * * *